United States Patent
Rufo et al.

(10) Patent No.: US 11,566,924 B2
(45) Date of Patent: Jan. 31, 2023

(54) MODULAR SENSING DEVICE, SYSTEM, AND METHOD

(71) Applicant: Boston Engineering Corporation, Waltham, MA (US)

(72) Inventors: Michael Rufo, Hanover, MA (US); Michael Conry, Beverly, MA (US); Robert Watson, Lowell, MA (US)

(73) Assignee: Boston Engineering Corporation, Waltham, MA (US)

(*) Notice: Subject to any disclaimer, the term of this patent is extended or adjusted under 35 U.S.C. 154(b) by 41 days.

(21) Appl. No.: 17/144,527

(22) Filed: Jan. 8, 2021

(65) Prior Publication Data

US 2021/0215518 A1 Jul. 15, 2021

Related U.S. Application Data

(60) Provisional application No. 62/959,513, filed on Jan. 10, 2020.

(51) Int. Cl.
| | | |
|---|---|---|
| *G01D 11/24* | (2006.01) | |
| *G01D 21/02* | (2006.01) | |
| *G06F 8/61* | (2018.01) | |
| *B63B 22/00* | (2006.01) | |
| *B63B 22/08* | (2006.01) | |
| *B63C 7/26* | (2006.01) | |

(52) U.S. Cl.
CPC .......... *G01D 11/245* (2013.01); *B63B 22/003* (2013.01); *B63B 22/08* (2013.01); *G01D 21/02* (2013.01); *G06F 8/61* (2013.01); *B63B 2022/006* (2013.01); *B63C 7/26* (2013.01)

(58) Field of Classification Search
CPC ........ G01D 11/245; G01D 21/02; G06F 8/61; G01N 33/1886; G01N 2201/0218
See application file for complete search history.

(56) References Cited

U.S. PATENT DOCUMENTS

| | | | |
|---|---|---|---|
| 3,906,565 A | | 9/1975 | Dorrance et al. |
| 5,209,112 A | * | 5/1993 | McCoy ................ B63B 22/003 73/170.01 |
| 6,772,705 B2 | | 8/2004 | Leonard et al. |
| 6,807,856 B1 | | 10/2004 | Webb |
| 8,397,658 B1 | | 3/2013 | Imlach et al. |
| 10,638,742 B1 | * | 5/2020 | Barnett ................ A01K 97/125 |
| 11,346,690 B2 | * | 5/2022 | Cardenas ................ B63B 22/08 |
| 2011/0309823 A1 | * | 12/2011 | Palassis ................ G01D 11/245 324/149 |
| 2014/0047682 A1 | | 2/2014 | Blackman et al. |
| 2018/0162501 A1 | * | 6/2018 | Peterson ................ B63B 22/18 |
| 2019/0170720 A1 | * | 6/2019 | Howard ............ G01N 33/1886 |

(Continued)

FOREIGN PATENT DOCUMENTS

| | | |
|---|---|---|
| CN | 105444743 | 3/2016 |
| CN | 109059876 | 12/2018 |
| CN | 110207673 | 9/2019 |

(Continued)

*Primary Examiner* — Francis C Gray
(74) *Attorney, Agent, or Firm* — BainwoodHuang

(57) ABSTRACT

A technique provides a modular sensing device having multiple separable modules attached end to end. The modules are selectable based on mission requirements, with different modules and combinations thereof selected for different mission types and/or requirements.

22 Claims, 7 Drawing Sheets

(56) References Cited

U.S. PATENT DOCUMENTS

2019/0353572 A1* 11/2019 Ning ..................... G01N 15/02

FOREIGN PATENT DOCUMENTS

| FR | 2834557 | 7/2003 |
|----|---------|--------|
| FR | 2969281 | 6/2012 |
| RU | 2609849 | 2/2017 |
| WO | 03067021 | 8/2003 |
| WO | 2012013962 | 2/2012 |
| WO | 2018067738 | 4/2018 |
| WO | 2021126836 | 6/2021 |

* cited by examiner

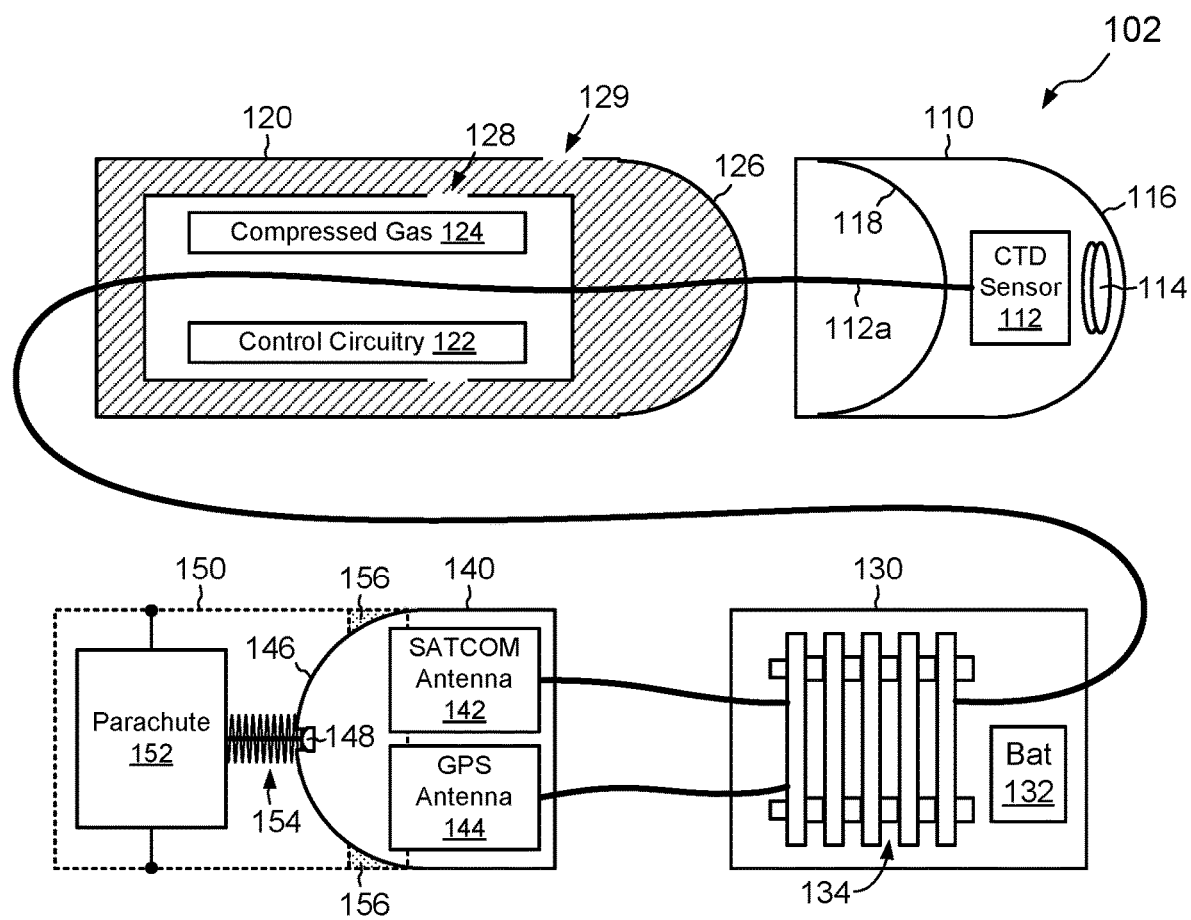
*FIG. 2*
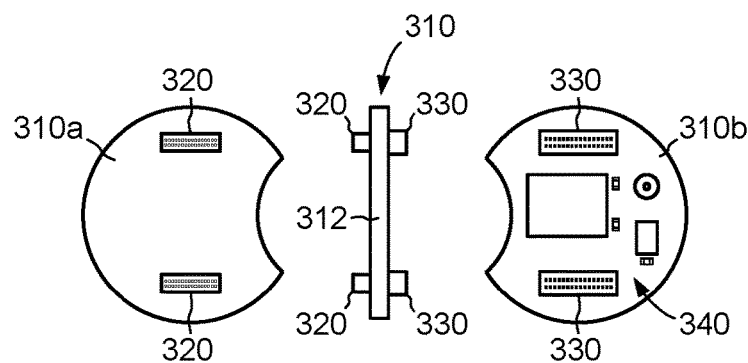
*FIG. 3A*   *FIG. 3B*   *FIG. 3C*

MODULAR SENSING DEVICE, SYSTEM, AND METHOD

STATEMENT REGARDING FEDERALLY SPONSORED RESEARCH OR DEVELOPMENT

This invention was made with government support under WC-133R-15-CN-0112 awarded by the National Oceanic and Atmospheric Administration. The government has certain rights in the invention.

BACKGROUND

Hurricanes in the United States cause damages of $1 to $3 billion annually with an average death rate of nearly 20 persons. In a typical year having three hurricanes, the total cost of warning and emergency response is nearly $800 million, which is approximately $0.5 to $1.0 million per mile of coast line. Hurricane Katrina, which made landfall on the Gulf Coast of the United States in 2005, caused an estimated $100 billion in damage and economic losses as high as $250 billion.

Accurate measurements in and around hurricanes are critical for predicting hurricane intensity, and thus the severity of risks posed to human life and property. Current approaches to measuring hurricane-related factors employ buoys, sondes, and dropsondes. Buoys are floating devices that make measurements near the surface of a body of water and store collected data, which may be retrieved directly by visiting the buoys or by receiving the data over a wireless link. Sondes are devices that operate within a body of water and collect data as they descend. Relevant data may include conductivity, temperature, and depth, for example. Dropsondes are sondes adapted for deployment from an aircraft. A dropsonde can measure atmospheric conditions while falling through the air. After splashdown, a dropsonde can measure water conditions as it sinks through the water. Sondes and dropsondes may log their data while operating under water and transmit the logged data upon resurfacing. Some sondes and dropsondes may perform "profiling," i.e., controllably rising and sinking to various depths and measuring water columns at different locations.

SUMMARY

Unfortunately, environmental sensing devices such as buoys, sondes, and dropsondes tend to be highly specialized assemblies adapted for particular sensors and/or payloads. Such devices tend to be either single use or multiuse at high cost. In addition, there is currently no inexpensive dropsonde capable of making diverse measurements of atmospheric or ocean conditions, features which are essential in predicting the intensity of hurricanes.

In contrast with conventional sensing devices, an improved technique provides a modular sensing device having multiple separable modules attached end to end. The modules are selectable based on mission requirements, with different modules and combinations thereof selected for different mission types and/or requirements.

In some examples, the modules or a subset thereof conform to a common mechanical attachment specification, such that modules of different types and/or capabilities can be physically attached together.

In some examples, the modules or a subset thereof conform to a common electrical connector specification, such that modules of different types and/or capabilities can be electrically connected together.

In some examples, the modules or a subset thereof conform to a common software specification, such that modules of different types and/or capabilities can operate within a common software framework of the device.

Certain embodiments are directed to a modular sensing device configured to execute one or more underwater missions. The device includes multiple separable modules physically attached end-to-end and forming an elongated structure of the device. At least one of the modules is selected, from among multiple module choices, for inclusion in the device based on mission-specific requirements.

In some examples, the modules each have a cylindrical shape and attach together to form an elongated cylinder.

In some examples, a blind-mate electrical connection is formed between two adjacent modules of the device.

In some examples, the modules of the device include a nose module that houses a set of sensors configured to make underwater measurements, and an electronics module that houses electronic control circuitry configured to operate the device autonomously. In an example, the electronics module is electrically coupled to the nose module for receiving and storing the underwater measurements.

According to some examples, the nose module is disposed at one end of the device and includes a sensor for conductivity, temperature, and/or depth, and a set of openings configured to allow water to pass into the nose module.

In some examples, the nose module further includes a ballast weight.

According to some examples, the nose module further includes a set of sensors based on any of optical, acoustic, magnetic, inertial, and/or laser measurements.

According to some examples, the modules further includes a variable buoyancy module electrically coupled to the electronics module. The variable buoyancy module is configured to vary its own buoyancy in response to control signals from the electronics module.

In some examples, the variable buoyancy module is electrically coupled to the electronics module via multiple conductive paths that pass through at least one other module of the device.

In some examples, the electronics module includes multiple circuitboard assemblies arranged in a vertical stack. The circuitboard assemblies include (i) a first circuitboard assembly having a first connector that attaches to a second circuitboard assembly below the first circuitboard assembly in the stack and (ii) a second connector that attaches to a third circuitboard assembly above the first circuitboard assembly in the stack.

In some examples, an electrical bus extends to the first, second, and third circuitboard assemblies via the first and second connectors.

According to some examples, the modules further include a communications module that houses one or more antennas for wireless communications.

In some examples, the modules include a parachute module disposed at an end of the device, the parachute module being automatically detachable from the device.

In some examples, the modules include a nose module, a communications module, and a parachute module, and the communications module has a convex outer end disposed against the parachute module such that, upon separation of the parachute module from the device, the convex outer end of the communications module forms the second end of the device opposite the nose module and facilitates upward movement of the device in water.

In some examples, the separable modules include first and second modules attached together via a liquid impermeable seal.

According to some examples, the device further includes an adapter that connects the first and second modules. The adapter includes a first portion that extends into the first module and forms a first annular channel with an outer wall of the first module, and a second portion that extends into the second module and forms a second annular channel with an outer wall of the second module. The adapter is attached to the first module via a first cord inserted into the first annular channel, and the adapter is attached to the second module via a second cord inserted into the second annular channel.

According to some examples, the outer wall of the first module includes a first hole into which the first cord is inserted to attach the adapter to the first module. Also, in some examples, the outer wall of the second module includes a second hole into which the second cord is inserted to attach the adapter to the second module.

According to some examples, the first module is configured to detach from the adapter by withdrawal of the first cord from the first hole, and the second module is configured to detach from the adapter by withdrawal of the second cord from the second hole.

According to some examples, the device further includes a first O-ring disposed in a first half-annular channel between the first portion of the adapter and the outer wall of the first module, and a second O-ring disposed in a second half-annular channel between the second portion of the adapter and the outer wall of the second module. In an example, the first O-ring and the second O-ring provide the liquid-impermeable seal.

Other embodiments are directed to a modular sensing device configured to execute one or more underwater missions. The device includes multiple separable modules physically attached end-to-end and forming an elongated structure of the device. The modules include a nose module that houses a set of sensors, a variable buoyancy module configured to automatically vary buoyancy of the device, an electronics module that houses control circuitry, and a communications module that includes a set of antennas for wireless communication. At least one of the modules is selected, from among multiple module choices, for inclusion in the device based on mission-specific requirements.

Still other embodiments are directed to a method of configuring a modular sensing device for executing an underwater mission. The method includes receiving mission requirements, selecting a subset of modules to meet mission requirements from among a larger set of modules having respective functions and/or capabilities, installing software of at least one of the selected modules into memory of an electronics module of the selected modules, and connecting the selected modules end-to-end, including establishing liquid-impermeable seals between at least two of the modules and forming electrical connections between or among at least some of the modules.

The foregoing summary is presented for illustrative purposes to assist the reader in readily grasping example features presented herein; however, this summary is not intended to set forth required elements or to limit embodiments hereof in any way. One should appreciate that the above-described features can be combined in any manner that makes technological sense, and that all such combinations are intended to be disclosed herein, regardless of whether such combinations are identified explicitly or not.

BRIEF DESCRIPTION OF THE SEVERAL VIEWS OF THE DRAWINGS

The foregoing and other features and advantages will be apparent from the following description of particular embodiments, as illustrated in the accompanying drawings, in which like reference characters refer to the same or similar parts throughout the different views. The drawings are not necessarily to scale, emphasis instead being placed upon illustrating the principles of various embodiments.

FIG. 2 is a partially exploded view of the modular sensing device of FIG. 1.

FIGS. 3A-3C are rear, side, and front plan views, respectively, of an example circuit assembly used in an electronics module of FIGS. 1 and 2.

DETAILED DESCRIPTION

Embodiments of the improved technique will now be described. One should appreciate that such embodiments are provided by way of example to illustrate certain features and principles but are not intended to be limiting.

An improved technique provides a modular sensing device having multiple separable modules attached end to end. The modules are selectable based on mission requirements, with different modules and combinations thereof selected for different mission types.

Figure 1:
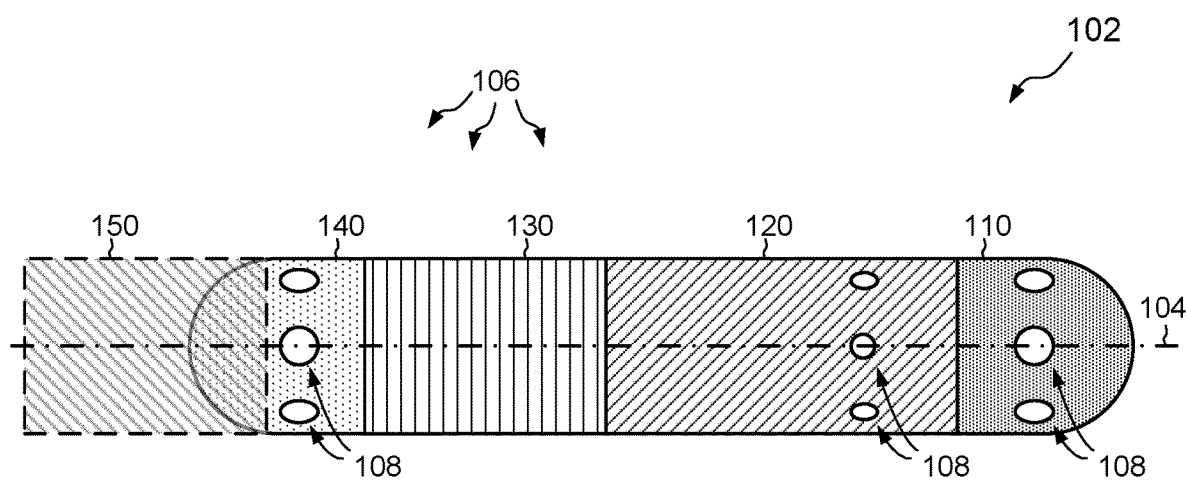
FIG. 1 is a front plan view of an example modular sensing device in accordance with certain embodiments.

FIG. 1 shows an example modular sensing device 102 according to certain embodiments. Here, multiple separable modules 106 are arranged end-to-end along an axis 104 of the device 102. The depicted modules 106 include a nose module 110, a variable buoyancy module 120, an electronics module 130, a communications module 140, and a parachute module 150. Other embodiments may include a greater or lesser number of modules 106, and such modules may be of different types and/or capabilities than those shown. The depicted example is merely illustrative.

Certain modules, such as nose module 110, variable buoyancy module 120, and communications module 140, may include holes 108 or other openings to allow water to pass freely in and out. Other modules, such as electronics module 130, may be configured to block liquid from entering.

FIG. 2 shows the device 102 in additional detail. Here, nose module 110 includes environmental sensors, such as a CTD (conductivity, temperature, and depth) sensor 112, and ballast (e.g., weights) 114. Some embodiments do not require CTD sensors but rather may measure conductivity, temperature, or depth, or any combination thereof. The ballast 114 assists in keeping the nose module, 110 pointing down and the device 102 vertical when the device 102 is submerged in water. Nose module 110 has a convex outer surface 116, which may be hemispherically shaped, for example, to enable the device 102 to descend smoothly under water. In some examples, nose module 110 has a concave inner surface 118 adapted for receiving a convex (e.g., hemispherical) outer surface 126 of variable buoyancy module 120.

The variable buoyancy module 120 may have a convex outer surface 126 even though it is not positioned at an end of the device 102. By doing so, the same type of module may be used in other devices as first or last modules. The convex outer surface 126 of the variable buoyancy module 120 thus promotes modularity. Although other modules 106 are shown with flat ends, one should appreciate that those modules may have rounded ends in certain embodiments, so that they may perform well when placed at the ends of devices in which they are installed.

Variable buoyancy module 120 is configured to vary its own buoyancy, and hence the buoyancy of the overall device 102, in response to electronic control. To this end, variable buoyancy module 120 may in some examples include control circuitry 122, such as a microcontroller, microprocessor, or the like, and a source of compressed gas 124, such as a $CO_2$ cartridge or other gas source. Variable buoyancy module 120 may further include apertures 128 and 129 and associated valves (not shown) and other hardware. In response to control signals, e.g., from the electronics module 130, the variable buoyancy module 120 is configured to displace water with gas within its envelope, or to displace gas with water, to controllably vary its gas-to-water ratio and thus its buoyancy, enabling the device 102 to controllably rise and fall within a water column.

Electronics module 130 is connected to the variable buoyancy module and includes, for example, a power source such as a battery 132 and an electronics assembly 134. As shown, the electronics assembly 134 is electrically connected to the CTD sensor 112 (and/or any environmental sensors in the nose module 110), e.g., via a cable that passes through the variable buoyancy module 120. Alternatively, connection to the CTD sensor 112 can be achieved in a more standard way, such as by using connectors between adjacent modules, e.g., in the manner described in connection with FIG. 5. In some examples, the electronics assembly 134 includes a microcontroller, microprocessor, or the like, as well as associated memory. It may further include an IMU (inertial measurement unit) and electronics for supporting GPS, SATCOM, and/or RF communications, such as interfaces to antennas provided in the communications module 140. In some examples, the power source may be provided in some other module, such as in the variable buoyancy module 120 or in a separate module (e.g., a battery module). Including the power source in the electronics module 130 is therefore merely illustrative.

In the example shown, communications module 140 includes a satellite communications (SATCOM) antenna 142 and a GPS (Global Positioning System) antenna 144, each of which may be electrically connected to the circuit assembly 134 via respective cables. In some examples, one or more RF (Radio Frequency) antennas may be provided, to support RF communication. Communications module 140 may preferably have a convex outer surface 146, e.g., for facilitating upward movement of the device 102 through water after separation of the parachute module 150. The convex outer surface 146 is preferably made of a non-conductive material, such as polyvinyl chloride (PVC) or chlorinated PVC (CPVC), to allow electromagnetic signals to and from antennas 142 and 144 to readily pass therethrough. The convex outer surface 146 is adapted to mate with a partially-concave inner surface 156 in the parachute module. In some examples, the communications module 140 may include an extendible mast (not shown) with antennas disposed at a remote end and/or along a length thereof. The extendable mast may serve to raise antennas away from the water surface to improve signal strength.

Parachute module 150 preferably has a detachable connection to communications module 140. For example, a pin 148 in the communications module 140 holds the parachute module 150 in place. Spring 154 applies a biasing outward force, which would separate the parachute module 150 from the communications module 140 but for the pin 148. In an example, the pin 148 (and/or its abutment within the communications module 140) is made of a water-soluble material, which is configured to melt or otherwise lose rigidity upon sustained contact with water, causing separation of the parachute module 150 from the communications module 140.

FIGS. 3A-3C show various views of an example circuit assembly 310, which forms a component of the electronics assembly 134 of FIG. 2. For example, multiple circuit assemblies (e.g., printed circuit boards) 310 of like size and shape may be stacked to form electronics assembly 134. As shown, each circuit assembly 310 has a substrate 312 (e.g., fiberglass, ceramic, or the like), which has a first side 310a and a second side 310b. Components 340 may be placed on one or both sides. In the example shown, the first side 310a has a pair of female connectors 320 mounted thereon and the second side 310b has a pair of male connectors 330. The female connectors 320 on one circuit assembly 310 are configured to engage the male connectors 330 on an adjacent circuit assembly 310 to form a vertical stack. Any number of circuit assemblies 310 may be stacked in this fashion, e.g., according to the requirements of the device 102.

Different circuit assemblies 310 may have different components and functionality. For example, one circuit assembly 310 may be specialized for SATCOM communication, while another circuit assembly 310 may be specialized for GPS. Other circuit assemblies 310 may be provided for other module-specific functions, the particular features of which may depend on the modules used. In addition, one or more circuit assemblies 310 may be provided for data processing, memory, and any other control circuitry needed for operating the device 102.

One should appreciate that the connectors 320 and 330 may provide a common bus that extends across some or all circuit assemblies 310 in the electronics assembly 134. The common bus may provide power, data, and control signals, for example, to enable a processor on one circuit assembly 310 to communicate with and control other circuit assemblies 310. Although the electronics assembly 134 shown in FIG. 2 includes five circuit assemblies 310, one should appreciate that the number of circuit assemblies 310 in a given device 102 may be greater or fewer than five.

Figure 4A:
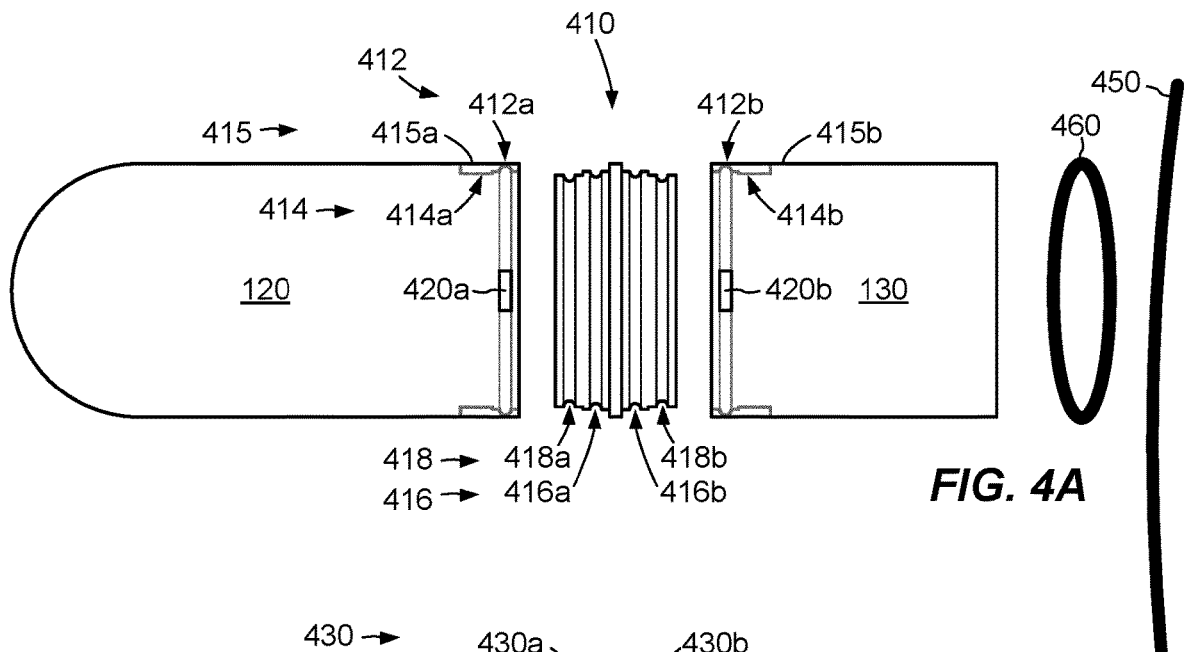
FIGS. 4A and 4B are front plan views of an example physical connection for connecting two of the modules shown in FIGS. 1 and 2.
Figure 4B:
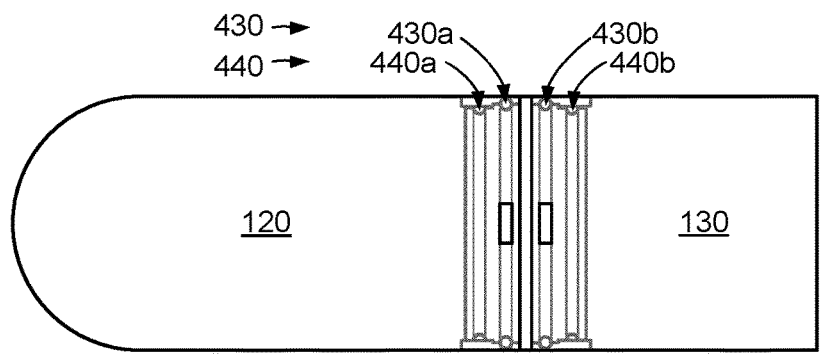

FIGS. 4A and 4B show an example arrangement for physically connecting two adjacent modules 106 to form a secure and liquid-impenetrable connection. As shown, an adapter 410 is placed between the modules 106, with the modules in this case being the variable buoyancy module 120 and the electronics module 130, for example. Adapter 410 has left and right ends (from the perspective of the figure) with external grooves 416 (e.g., 416a and 416b) and 418 (e.g., 418a and 418b) formed thereon. Modules 120 and 130 have respective ends with internal grooves 412 (e.g., 412a and 412b) and smooth surfaces 414 (e.g., 414a and 414b). As shown, the grooves 412 and smooth surfaces 414 may be provided on inner surfaces of outer walls 415 (e.g., 415a and 415b) of the respective modules. When assembled, external grooves 416 on adapter 410 align with internal grooves 412 in modules 106 to form annular channels 430 (430a and 430b). Also, the external grooves 418 on the adapter 410 align with smooth surfaces 414 in the modules 106 to form half-annular channels 440 (440a and 440b). Channels 430 are configured to receive respective cords 450, and channels 440 are configured to receive respective O-rings 460.

To form a secure and liquid impenetrable connection, O-rings 460 may be applied onto respective grooves 418 of adapter 410. Modules 120 and 130 may then be applied over respective ends of the adapter 410, such that one O-ring 460 sits within the half-annular channel 440a and another O-ring 460 sits within the half-annular channel 440b. The half-annular channels 440 tend to compress the O-rings 460 against the smooth, flat surfaces 414, such that each O-ring 460 provides a seal that extends all the way around. For inserting cords 450, holes 420a and 420b extend into respective channels 430a and 430b. One cord 450 may be inserted into hole 420a and pushed through channel 440a until its end wraps around and aligns with the same hole. Likewise, another cord 450 may be inserted into hole 420b and pushed through channel 440b until the end of that cord wraps around and aligns with hole 420b. Each cord 450 preferably has a length that is approximately the same as the circumference of the channels 430.

Cords 450 may be composed of a relatively incompressible material, such as nylon, aluminum-reinforced nylon, or other polymers or metals. O-rings 460 may be composed of a more compressible material, such as rubber, neoprene, nitrile, silicone, or the like. With the two modules 106 attached via the adapter 410, cords 450 hold the modules rigidly to the adapter 410 and O-rings 460 prevent liquid from passing across channels 440. A secure and liquid-impenetrable attachment is thus formed.

In an example, the attachment arrangement of FIGS. 4A and 4B is standardized across numerous modules of different types and capabilities. Such standardization enables a variety of modules to be physically attached together, thereby promoting modularity in the device 102.

In an alternative connection arrangement, the modules 106 may individually be capped at both ends, so as to seal them from one another. Modules 106 may then be attached together end to end using a cord or other scheme. The particular arrangement as shown in FIGS. 4A and 4B is therefore not intended to be limiting.

Figure 5:
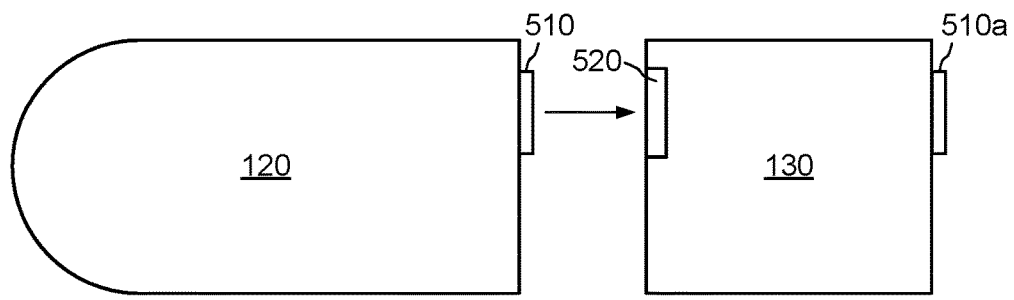
FIG. 5 is a front plan view of an example blind-mate electrical connector arrangement for electrically connecting two of the modules shown in FIGS. 1 and 2.

FIG. 5 shows an example electrical connector arrangement between adjacent modules 106. The arrangement of FIG. 5 may be used with the physical connectors of FIGS. 4A and 4B, but this is not required. In the example shown, electrical connector 510 is configured to mate with electrical connector 520. For example, connector 510 may include pins that engage respective sockets in connector 520, or vice-versa, enabling power and electrical signals to pass between the modules, such as modules 120 and 130, for example. According to certain examples, connectors 510 and 520 form a blind-mate connection, such that physically attaching the two modules 120 and 130 (e.g., using the arrangement of FIGS. 4A and 4B) causes the connectors 510 and 520 to mate. With this arrangement, electrical connections between adjacent modules are made automatically as a result of establishing physical connections.

In an example, the connector arrangement of FIG. 5 is standardized, such that any two adjacent modules of any kind or capability may be connected as shown. For example, connector 510a on module 130 may be configured to mate with a connector (like 520) on some other module. Within module 130, some or all connector contacts on connector 520 may internally connect to corresponding contacts in connector 510a, effectively forming a device bus that extends across multiple modules.

Figure 6A:
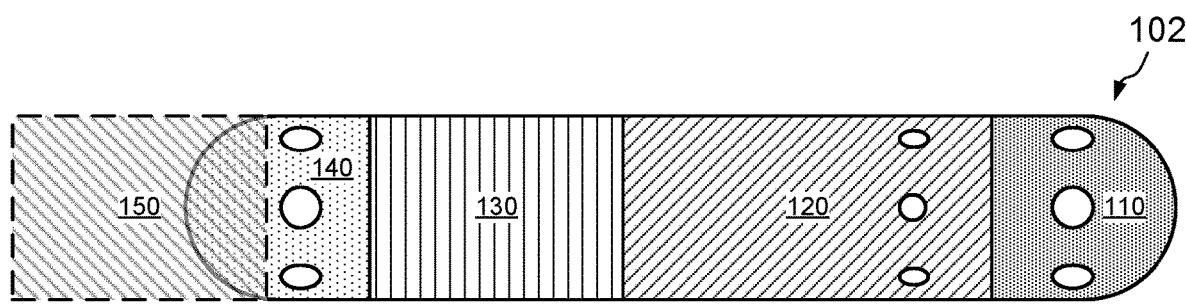
FIGS. 6A-6D are front plan views of various sensing devices formed from different combinations of modules.
Figure 6B:
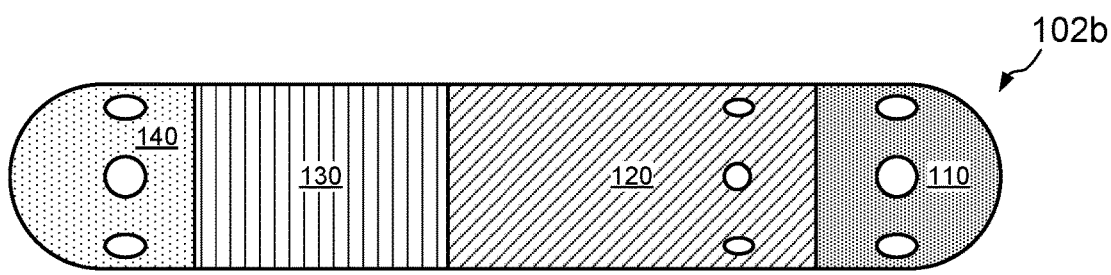
Figure 6C:
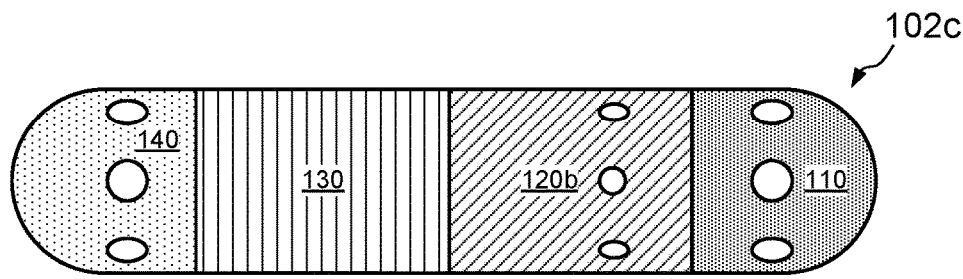
Figure 6D:
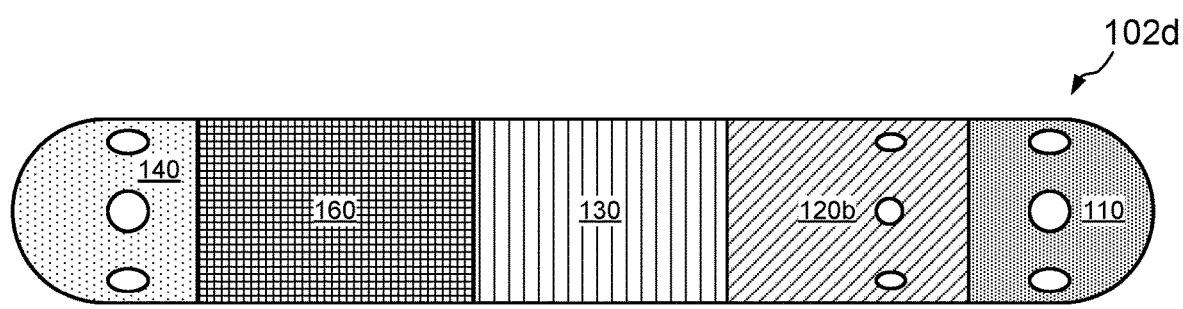

FIGS. 6A-6D show various device configurations having respective combinations of modules 106. The FIG-6A arrangement shows the same device 102 as was shown in FIG. 1, with the same modules, i.e., a nose module 110, a variable buoyancy module 120, an electronics module 130, a communications module 140, and a parachute module 150. In FIG. 6B, device 102b is similar to device 102 but has no parachute module 150. For example, device 102b may be a sonde, whereas device 102 may be dropsonde. In FIG. 6C, device 102c is similar to device 102b but is equipped with a variable buoyancy module 120b having different capabilities from those of the variable buoyancy module 120. For example, the variable buoyancy module 120b it may be designed for shallower submersion. FIG. 6D shows a device 102d which is similar to device 102c, but device 102d includes an extra module 160, such as a battery (or extra battery) or other special-purpose hardware. These are merely a few of the myriad possible ways that modules 106 may be arranged to form a device 102.

Figure 7:
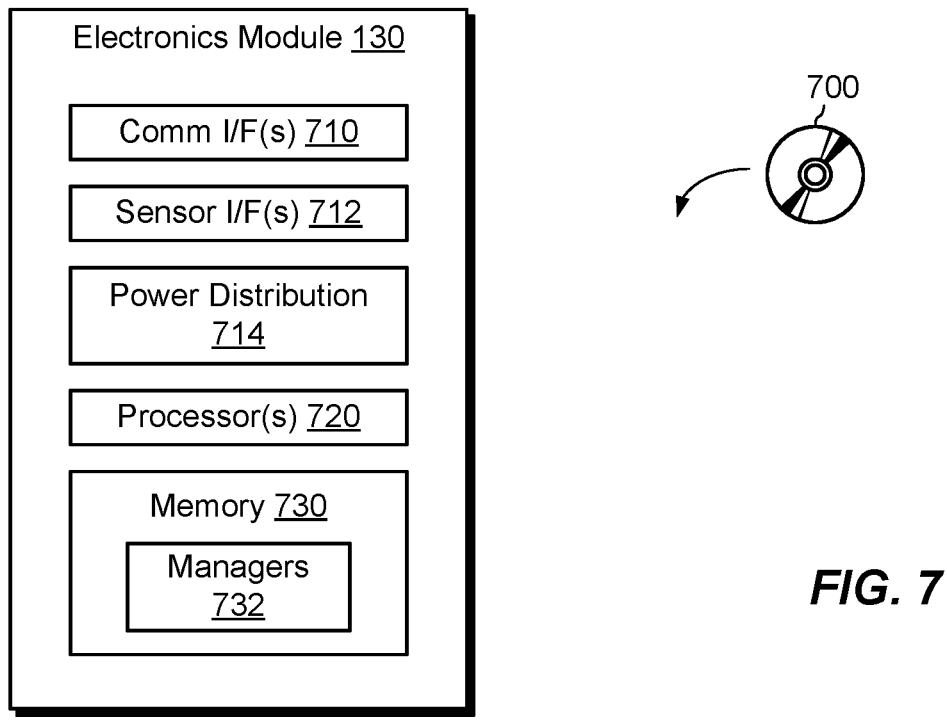
FIG. 7 is a block diagram showing example aspects of an electronics module of FIGS. 1 and 2.

FIG. 7 shows example constituents of the electronics module 130 in additional detail. Here, the electronics module 130 includes, e.g., on circuit assemblies 310 (FIG. 3), one or more communication interfaces 710 (e.g., SATCOM and GPS interfaces), one or more sensor interfaces 712 (e.g., interface to CTD sensor 112; FIG. 2), power distribution circuitry 714 (e.g., battery 132 and associating switches), a set of processors 720, and memory 730. The set of processors 720 includes one or more processing chips and/or assemblies, such as a microcontroller or microprocessor and associated digital hardware. The memory 730 includes both volatile memory, e.g., RAM (Random Access Memory), and non-volatile memory, such as one or more ROMs (Read-Only Memories), magnetic disk drives, flash drives, solid state drives, and the like. The memory 730 further includes various software managers 732, for managing operation of the device 102. The set of processors 720, memory 730, and associated hardware together form control circuitry, which is constructed and arranged to carry out various methods and functions as described herein. Also, the memory 730 includes a variety of software constructs realized in the form of executable instructions. When the executable instructions are run by the set of processors 720, the set of processors 720 carry out the operations of the software constructs. Although certain software constructs are specifically shown and described, it is understood that the memory 730 typically includes many other software components, which are not shown, such as an operating system, various applications, processes, and daemons. In some examples, the operating system may be provided as an RTOS (real-time operating system).

The improvement or portions thereof may be embodied as a computer program product including one or more non-transient, computer-readable storage media 700, such as a magnetic disk, magnetic tape, compact disk, DVD, optical disk, flash drive, solid state drive, SD (Secure Digital) chip or device, Application Specific Integrated Circuit (ASIC), Field Programmable Gate Array (FPGA), and/or the like. Any number of computer-readable media may be used. The media may be encoded with instructions which, when executed on one or more computers or other processors, perform the process or processes described herein. Such media may be considered articles of manufacture or machines, and may be transportable from one machine to another.

Figure 8:
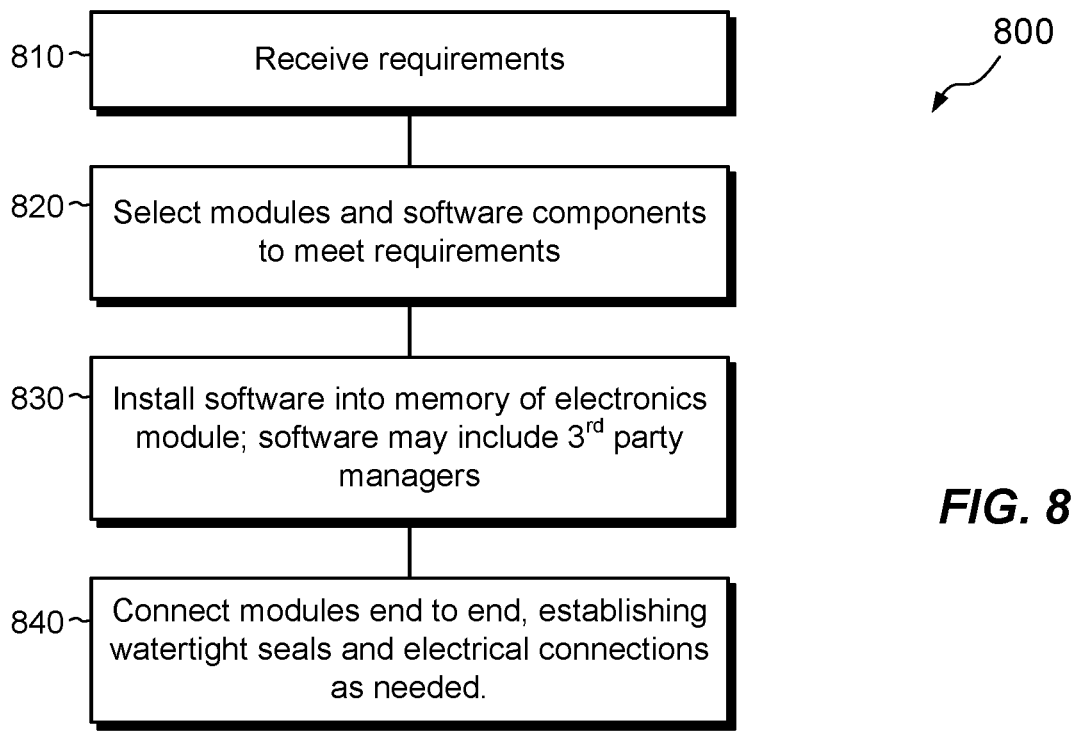
FIG. 8 is a flow chart showing an example method of providing a modular sensing device based on a set of requirements.

FIG. 8 shows an example method 800 of constructing a modular sensing device 102. The method 800 may be carried out by a manufacturer, distributor, end user, or any other person or entity. In some examples, the method 800 may be carried out automatically or semi-automatically, e.g., by machine, and the acts of method 800 may be conducted in an order different from that illustrated, including performing some acts simultaneously.

At 810, requirements of a modular sensing device are received. The requirements may include, for example, a designation as to whether the device is a buoy, a sonde, or a dropsonde. The requirements may also include specifications, such as maximum depth of operation, desired speed of ascent or descent through water, supported communications (e.g., SATCOM, cellular data, etc.), mission duration, and any other information relevant to intended operation.

At 820, modules and software components are selected to address the received requirements. For example, if device is specified as a dropsonde, a parachute module 150 may be selected. A larger parachute module may be selected for a larger dropsonde. A particular communications module may be selected based on the communications required, and an electronics module may be selected having a particular number and selection of circuit assemblies 310. More generally, many modules may be available, providing various types of functionality and/or having various capabilities, but only a subset of such modules are selected for inclusion in the device.

At 830, software is installed in electronics module 130 for controlling the selected modules. Overall mission software may also be installed to orchestrate activities of the device 102 during its intended mission.

At 840, the selected modules 102 are connected end to end, establishing liquid-impenetrable seals (e.g., FIGS. 4A and 4B) and forming electrical connections (e.g., FIG. 5), where needed.

Figure 9:
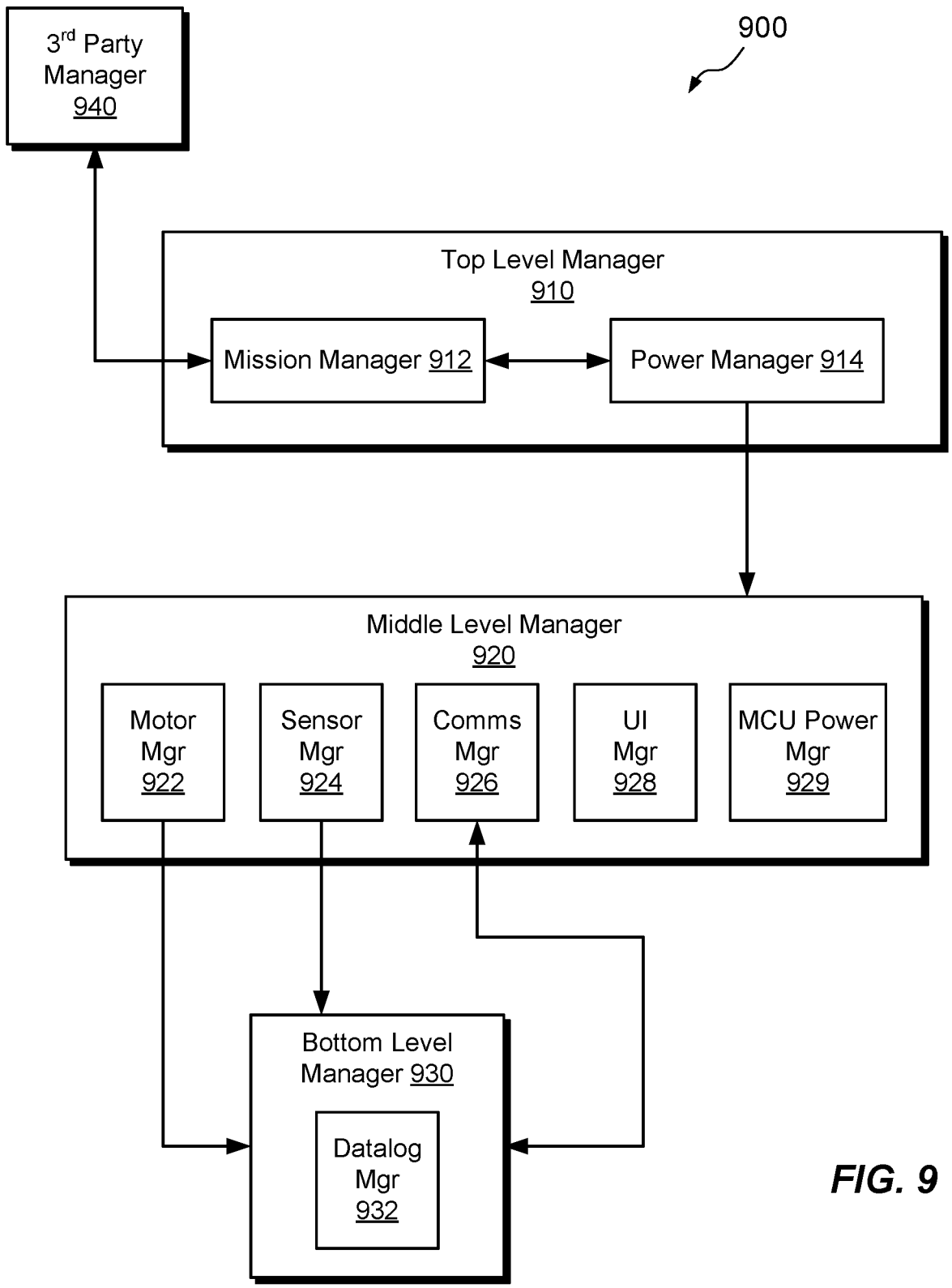
FIG. 9 is a block diagram of an example software structure for operating the modular sensing device of FIGS. 1 and 2.

FIG. 9 shows an example arrangement 900 of software constructs that may be operated in a device 102, e.g., the set of processors 720 of the electronics module 130. The arrangement 900 may be designed with modularity and flexibility in mind. For example, the arrangement 900 may provide an open architecture having a standard API (Application Program Interface). Third parties may develop code for modules or missions that plug in to the arrangement 900 with minimal adjustment. As shown, the arrangement 900 may be provided in the form of a top level manager 910, a middle level manager 920, and a bottom level manager 930.

Top level manager 910 may include an overall mission manager 912 and a power manager 914. The mission manager 912 orchestrates a mission plan for the device 102, and the power manager 914 controls the distribution of electrical power to one or more of the other modules 102. The power manager 914 may also control a power mode of the device 102, e.g., when the processor(s) 720 enter and exit a sleep state or some other low-power mode. In some examples, a third party manager 940 coordinates with the mission manager 912 to assist with mission orchestration.

Middle level manager 920 includes individual managers for different modules and their components, and may include, for example, motor manager 922, sensor manager 924, communications manager 926, UI (User Interface) manager 928, and MCU (Micro Controller Unit) power manager 929. Different middle level managers may be provided for different module selections.

Bottom level manager 930 may include a data logging manager 932. For example, the electronics module 130 may log data collected while the device 102 operates under water and then transmit its data wirelessly to a remote receiver (via communications module 140) upon resurfacing.

Figure 10:
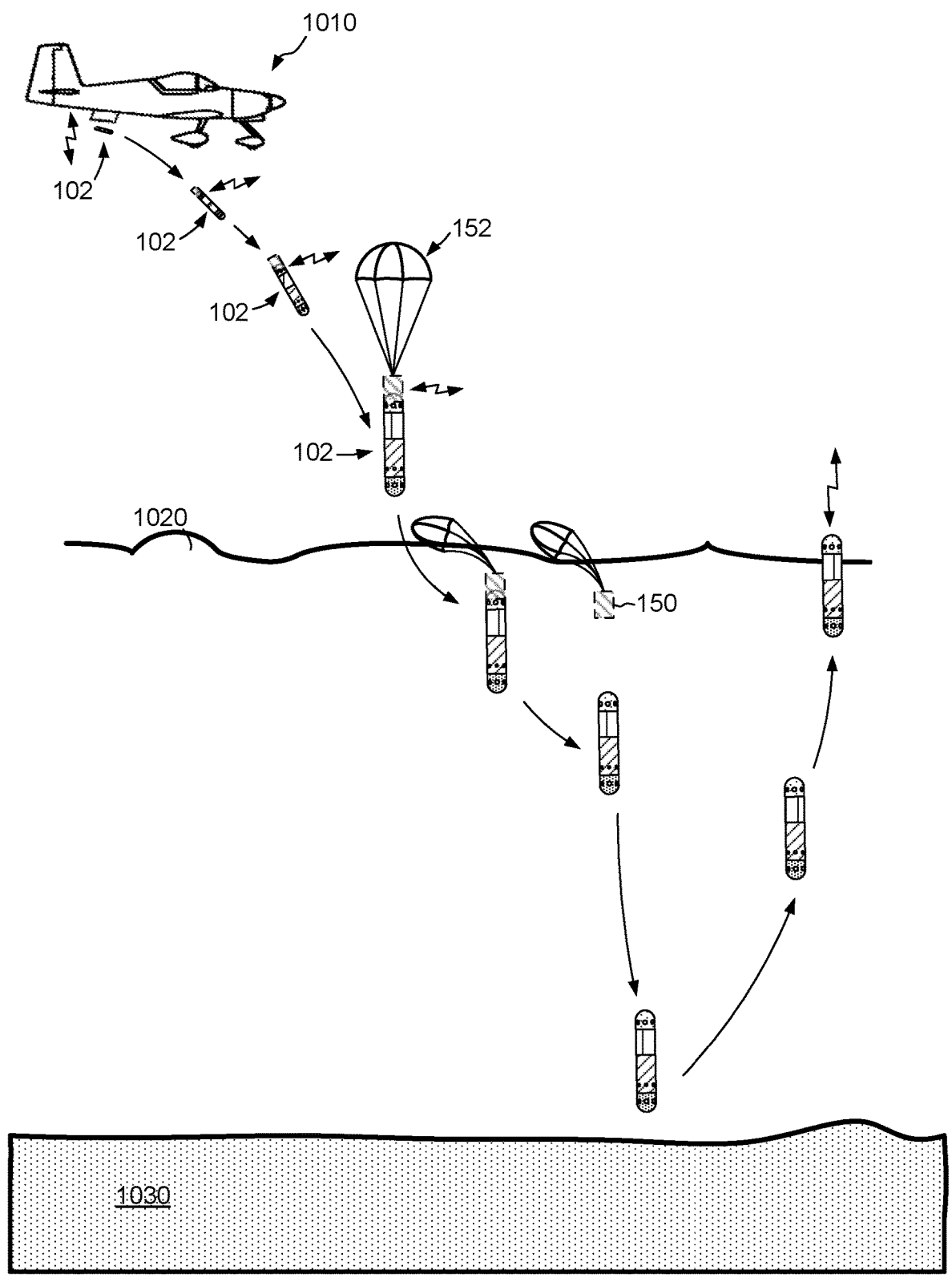
FIG. 10 is a diagram showing an example mission deployment of a modular sensing device.

FIG. 10 shows an example deployment of a modular sensing device 102. As shown, an airplane 1010 drops or otherwise dispenses a device 102, which begins falling through the air. Ballast 114 causes the device 102 to fall nose-first, i.e., with nose module 110 pointing down. Parachute 152 opens, and device 102 begins a slowed descent. Depending on application, the device 102 may monitor environmental factors of the air, such as temperature, pressure, humidity, particulate matter, and so forth, as it descends through the atmosphere. Device 102 may also monitor its own location and altitude, e.g., using GPS. Device 102 may data log the results and/or transmit the results, e.g., via SATCOM, to a remote receiver (not shown). Device 102 eventually splashes down, striking the surface 1020 of a body of water. In some examples, the device 102 collects surface data at this time. Assuming the device 102 is configured for sub-surface operation, then, after a period of contact with water, the parachute module 150 disengages from the device 102. The device 102 then begins to descend toward the floor 1030 of the body of water, continuing to log data as it goes. For example, device 102 may repeatedly measure conductivity, temperature, and depth. Depending on the mission, the device 102 may perform profiling, e.g., by action of the variable buoyancy module 120, alternately ascending and descending and making measurements of different water columns. Once measurements have been made, device 102 ascends to the surface 1020, whereupon device 102 transmits its data log wirelessly to a receiver. Alternatively, the device 102 may be retrieved and its data may be read directly.

An improved technique has been described that provides a modular sensing device 102 having multiple separable modules 102 attached end to end. The modules 102 are selectable based on mission requirements, with different modules and combinations thereof selected for different mission types. Modules 102 may connect to other modules using a common physical connection scheme, such as the one shown in FIGS. 4A and 4B, and may connect electrically using a common connector scheme, such as that shown in FIG. 5. In addition, device 102 may have a software architecture that includes an open API such that new modules are easily incorporated and new missions are easily specified by others beside the original equipment manufacturer.

Having described certain embodiments, numerous alternative embodiments or variations can be made. For example, although embodiments have been described in connection with environmental and/or underwater sensing for monitoring hurricane activity, the invention is not so limited. Rather, embodiments can be constructed with other ends in mind, the aspects and particulars of which are not critical to the invention.

As used throughout this document, the words "comprising," "including," "containing," and "having" are intended to set forth certain items, steps, elements, or aspects of something in an open-ended fashion. Also, as used herein and unless a specific statement is made to the contrary, the word "set" means one or more of something. This is the case regardless of whether the phrase "set of" is followed by a singular or plural object and regardless of whether it is conjugated with a singular or plural verb. Also, a "set of" elements can describe fewer than all elements present. Thus, there may be additional elements of the same kind that are not part of the set. Further, ordinal expressions, such as "first," "second," "third," and so on, may be used as adjectives herein for identification purposes. Unless specifically indicated, these ordinal expressions are not intended to imply any ordering or sequence. Thus, for example, a "second" event may take place before or after a "first event," or even if no first event ever occurs. In addition, an identification herein of a particular element, feature, or act as being a "first" such element, feature, or act should not be construed as requiring that there must also be a "second" or other such element, feature or act. Rather, the "first" item may be the only one. Also, and unless specifically stated to the contrary, "based on" is intended to be nonexclusive. Thus, "based on" should not be interpreted as meaning "based exclusively on" but rather "based at least in part on" unless specifically indicated otherwise. Although certain embodiments are disclosed herein, it is understood that these are provided by way of example only and should not be construed as limiting.

Those skilled in the art will therefore understand that various changes in form and detail may be made to the embodiments disclosed herein without departing from the scope of the disclosure.

Additional Information:

Competition exists in air monitoring environments and in marine environments. The multi-modal variant of device 102 provides customers with one product that collects the information otherwise requiring two different devices (e.g., sondes) from existing suppliers, the cost of which are higher than our one product.

There are many variations of oceanic sensing devices, buoys, etc. Most of these are either single use and low cost, or long duration and high cost. Additionally many are very large and expensive to both deploy and use. Most devices that exist in this space also are specific to a single size and sensor or other payload with which they collect data. As such our design is to have a modular, multiple profile, expendable if desired, small and air deployable, system that can use a variety of sensors and also be increased or decreased in size as necessary provide customers with many cost-effective options for current and future missions.

There are currently no inexpensive, expendable air-deployed monitoring systems (Dropsondes) that measure temperature, salinity and currents as a function of depth under the ocean's surface after collecting atmospheric data on its descent to the ocean surface—all important factors in predicting the intensity of hurricanes.

The ability of variants of the described embodiments to collect subsea data for hurricanes will provide forecasters with subsea temperature, conductivity, and water current. The temperature versus depth information gathered will be used to calculate thermal energy of the ocean. This data is used to forecast if the hurricane can be expected to gain or lose strength and how quickly. Our method will provide more valuable data than both current buoy systems which just measure the surface temperature of the ocean and subsea sensors which either do not profile or do profile but at far higher costs. Neither can specifically provide targeted and relevant data on the built-up power of a hurricane or other oceanographic phenomena based on underwater temperature gradients.

This disclosure promises to solve critical issues in other parts of weather prediction as well as influencing defense work related to antisubmarine warfare and mine countermeasures to qualify the water column, among others.

Design configurations range from sub 3-inch diameter to "A" size (roughly 5-inch) with larger and smaller diameter versions in the development roadmap. Modules are designed in collaboration with customers, but existing options include a parachute module, optimized low-cost, replaceable CTD sensor and a variable buoyancy system for multiple tetherless profiling actions (up/down). Options on the roadmap include mission-specific acoustic and optical sensors. A current version variable buoyancy subsystem enables multiple 200 m profiles. A gas-producing, high density power module option providing long duration missions (6 months+) is on the technology roadmap. The long duration power module provides secondary (redundant), or primary variable buoyancy, in future options.

Without limiting the generality of the foregoing, example design features that enable this modularity and family of products include the following:

- Data extraction from these systems using Python and specific tools in excel and Matlab that allow us to do the same extraction independent of data type, sensors, and microcontroller.
- A modular electronics stack (which includes a series of stackable, interfacing printed circuit boards (PCBs) on a common bus) that enables the generation of additional hardware and software additions to be added or removed to configure the systems as necessary. Most recently, we have generated hardware and software for a RF (radio frequency) communication method for communicating and programming these PCBs without hull penetrations or disassembly.
- A family of systems is enabled by the design of our communications antenna system that has been proven to be submersible (due to our mold/potting method) and functional across all platforms (designed and tuned for the smallest form factor and including the potting materials).
- Software to allow the system to apply its IMU (inertial measurement unit) for not just acceleration measurement collection but also for detecting launch and landing events plus both sea state and seafloor characterization. These events initiate software states for the functionality of the systems. The commonality of the IMU and versatility of this code allows this feature to provide various systems to be initiated the same way, independent of the manner of deployment or launch.
- Datalogging processes and procedures have been designed for data compression and ease of transmittal, independent of communication method (RF, SATCOM, hard wired). This enables any sonde in our family to be configured for various sensors without the risk of being unsuitable for the transmission of the related data.
- A reed-switch is used to power on and off the system. Its location is critical and was chosen for application across a range of variations/configurations. A reed switch is activated by adding or removing a magnet. In our case, removing a magnet completes a circuit, connecting the power to the main system. The use of a reed switch avoids the need for an expensive or large switch thereby reducing cost and complexity/size of the system.
- A sensor "nose" is used to integrate sensors easily into the system with only screws (though with more length than our current incarnation can support, can also use the simple cord attachment of the other modules). Our design provides this interface but also a manner for maximizing the quantity of available VBS (variable buoyancy system) volume. The features include a "sunken" section of the upper circumference to integrate the two volumes without violating the outer envelope.

A modular battery pack is included that uses single cells wired together or in the preferred implementation, a cylindrical, modular, and stackable pack that can be added within any size configuration and removed easily (similar to a cordless drill battery pack but cylindrical and 1000 foot submersible).

Embodiments are comprised of the following main modular subsystems: the sensor "nose", the variable buoyancy system, the electronics module, the communications module, and the parachute module. The combination of these modules provides one configuration of the device. The key differentiators for this are the variable buoyancy system and the parachute system. Additionally, our integration of a low-cost implementation for conductivity temperature and depth sensing provides a low-cost point. The parachute system may be removable. For example, it may deploy upon exiting a launch tube on the aircraft and self-detach once it hits the water. The variable buoyancy system is unique and low-cost, easy to use reload and upgrade, and really could be a product in and of itself. The communications system is comprised of a GPS antenna and an Iridium satellite communications antenna.

A preferred implementation is to include an encapsulated conductivity temperature and depth sensor and a sensor module at the front (or in this case the bottom) of the design which is then attached to the variable buoyancy system through which the batteries and the connectors to the sensors pass. Our modular electronics stack is easily upgradable and provides opportunity for additional payloads and electronics within the main hull. The variable buoyancy system attaches at one end of this main hull and the antennas within the communications system attach on the other. The parachute system connects to the communications system at the very end of the device. The device is launched from its launch tube parachute first, which allows the system to open cleanly and then decelerate appropriately for the water surface.

Embodiments could be used for several different applications. They could be scaled up or used at the current size to provide other types of data collection for oceanographic and bathymetric surveys, tank inspections, antisubmarine warfare hydrophone placement, or potentially construction or other application depth measurements in water columns ranging from rivers to open waters. It is modular in that it could be applied to several different uses.

Several tests have been completed on the performance of the device in its MASED (Multi-Purpose Above Surface/Below Surface Expendable Dropsonde) configuration; oceanographic profiling. These tests have occurred in test tanks as well as vertical tubes on-site at our facility, and in the field off of the boat as well as off of a bridge and out of an aircraft.

Embodiments of the invention ultimately can provide desired sensor data into and/or at the water surface, or underwater, as needed to support decision-making by collecting data that is currently unavailable across multiple applications. They have a low comparable cost with an extensible core and can displace existing products to market. Their low cost makes them affordable across many missions. Our modular design reduces the amount of engineering required to customize for these missions. Leveraging its open architecture enables more people to advance the capabilities of the core platform. The modular design also provides options for power sources and energy capacity allowing variable durations of usage from short (hours) to long durations (months or years).

What is claimed is:

1. A modular sensing device configured to execute one or more underwater missions, comprising:
   multiple separable modules physically attached end-to-end and forming an elongated structure of the device,
   at least one of the modules selected, from among multiple module choices, for inclusion in the device based on mission-specific requirements.

2. The device of claim 1, wherein the modules each have a cylindrical shape and attach together to form an elongated cylinder.

3. The device of claim 2, further comprising a blind-mate electrical connection formed between two adjacent modules of the device.

4. The device of claim 2, wherein the modules include:
   a nose module that houses a set of sensors configured to make underwater measurements; and
   an electronics module that houses electronic control circuitry configured to operate the device autonomously, the electronics module electrically coupled to the nose module for receiving and storing the underwater measurements.

5. The device of claim 4, wherein the nose module is disposed at one end of the device and includes:
   a sensor for measuring conductivity, temperature, and/or depth; and
   a set of openings configured to allow water to pass into and through the nose module.

6. The device of claim 5, wherein the nose module further includes a ballast weight.

7. The device of claim 5, wherein the nose module further includes a set of sensors based on any of optical, acoustic, magnetic, inertial, and/or laser measurements.

8. The device of claim 4, wherein the modules further include a variable buoyancy module electrically coupled to the electronics module, the variable buoyancy module configured to vary its own buoyancy in response to control signals from the electronics module.

9. The device of claim 8, wherein the variable buoyancy module is electrically coupled to the electronics module via multiple conductive paths that pass through the at least one other module of the device.

10. The device of claim 9, wherein the electronics module includes multiple circuitboard assemblies arranged in a vertical stack, the circuitboard assemblies including (i) a first circuitboard assembly having a first connector that attaches to a second circuitboard assembly below the first circuitboard assembly in the stack and (ii) a second connector that attaches to a third circuitboard assembly above the first circuitboard assembly in the stack.

11. The device of claim 10, wherein an electrical bus extends to the first, second, and third circuitboard assemblies via the first and second connectors.

12. The device of claim 1, wherein the modules include a communications module that houses one or more antennas for wireless communications.

13. The device of claim 1, wherein the modules include a parachute module disposed at an end of the device, the parachute module being automatically detachable from the device.

14. The device of claim 1, wherein the modules include a nose module, a communications module, and a parachute module, and the communications module has a convex outer end disposed against the parachute module such that, upon separation of the parachute module from the device, the convex outer end of the communications module forms the second end of the device opposite the nose module and facilitates upward movement of the device in water.

15. The device of claim 1, wherein the separable modules include first and second modules attached together via a liquid impermeable seal.

16. The device of claim 15, further comprising an adapter that connects the first and second modules, the adapter including:
   a first portion that extends into the first module and forms a first annular channel with an outer wall of the first module; and
   a second portion that extends into the second module and forms a second annular channel with an outer wall of the second module,
   wherein the adapter is attached to the first module via a first cord inserted into the first annular channel, and
   wherein the adapter is attached to the second module via a second cord inserted into the second annular channel.

17. The device of claim 16,
   wherein the outer wall of the first module includes a first hole into which the first cord is inserted to attach the adapter to the first module, and
   wherein the outer wall of the second module includes a second hole into which the second cord is inserted to attach the adapter to the second module.

18. The device of claim 17,
   wherein the first module is configured to detach from the adapter by withdrawal of the first cord from the first hole, and
   wherein the second module is configured to detach from the adapter by withdrawal of the second cord from the second hole.

19. The device of claim 16, further comprising:
   a first O-ring disposed in a first half-annular channel between the first portion of the adapter and the outer wall of the first module; and
   a second O-ring disposed in a second half-annular channel between the second portion of the adapter and the outer wall of the second module,
   the first O-ring and the second O-ring providing the liquid-impermeable seal.

20. A modular sensing device configured to execute one or more underwater missions, comprising:
   multiple separable modules physically attached end-to-end and forming an elongated structure of the device, the modules including:
      a nose module that houses a set of sensors;
      a variable buoyancy module configured to automatically vary buoyancy of the device;
      an electronics module that houses control circuitry; and
      a communications module that includes a set of antennas for wireless communication,
   at least one of the modules selected, from among multiple module choices, for inclusion in the device based on mission-specific requirements.

21. The device of claim 20, wherein at least two of the modules are connected via an adapter that forms a liquid-impermeable seal between said at least two of the modules.

22. A method of configuring a modular sensing device for executing an underwater mission, comprising:
   receiving mission requirements;
   selecting a subset of modules to meet mission requirements from among a larger set of modules having respective functions and/or capabilities;
   installing software of at least one of the selected modules into memory of an electronics module of the selected modules; and
   connecting the selected modules end-to-end, including establishing liquid-impermeable seals between at least two of the modules and forming electrical connections between or among at least some of the modules.

* * * * *